United States Patent [19]

Charmot et al.

[11] Patent Number: 5,178,947
[45] Date of Patent: Jan. 12, 1993

[54] MAGNETIZABLE COMPOSITE MICROSPHERES BASED ON A CROSSLINKED ORGANOSILICON POLYMER

[75] Inventors: Dominique Charmot, Paris; Andre Thibon, Savigny Sur Orge, both of France

[73] Assignee: Rhone-Poulenc Chimie, Cedex, France

[21] Appl. No.: 634,909

[22] Filed: Dec. 27, 1990

[30] Foreign Application Priority Data

Dec. 27, 1989 [FR] France .................. 89 17233

[51] Int. Cl.$^5$ .................. B32B 9/04; B32B 19/04; B32B 27/04
[52] U.S. Cl. .................. 428/405; 428/692; 523/212
[58] Field of Search .................. 428/405, 692; 523/212

[56] References Cited

U.S. PATENT DOCUMENTS

| | | | |
|---|---|---|---|
| 3,159,601 | 12/1964 | Ashby | 260/46.5 |
| 3,159,662 | 12/1964 | Ashby | 260/448.2 |
| 3,220,972 | 11/1965 | Lamoreaux | 260/46.5 |
| 3,296,291 | 1/1967 | Chalk et al. | 260/448.2 |
| 3,344,111 | 9/1967 | Chalk | 260/46.5 |
| 3,436,366 | 4/1969 | Modic | 260/37 |
| 3,480,555 | 11/1969 | Jackson | 252/62.56 |
| 3,715,334 | 2/1973 | Karstedt | 260/46.5 |
| 3,775,452 | 11/1973 | Karstedt | 260/429 R |
| 3,814,730 | 6/1974 | Karstedt | 260/46.5 |
| 3,928,629 | 12/1975 | Chandra et al. | 427/387 |
| 4,094,804 | 6/1978 | Shimoiizaka | 252/62.52 |
| 4,364,377 | 12/1982 | Smith | 128/1.5 |
| 4,554,088 | 11/1985 | Whitehead et al. | 252/62.54 |
| 4,628,037 | 12/1986 | Chagnon et al. | 436/526 |
| 4,672,040 | 6/1987 | Josephson | 436/526 |
| 4,695,392 | 9/1987 | Whitehead et al. | 252/62.54 |
| 4,695,393 | 9/1987 | Whitehead et al. | 252/62.54 |
| 4,698,302 | 10/1987 | Whitehead et al. | 435/94 |
| 4,946,893 | 8/1990 | Saito et al. | 524/862 |
| 4,985,166 | 1/1991 | Leising et al. | 252/62.54 |
| 5,034,145 | 7/1991 | Leising et al. | 252/62.54 |

FOREIGN PATENT DOCUMENTS

0125995A3 11/1984 European Pat. Off. .
0319828A2 6/1989 European Pat. Off. .

Primary Examiner—Edith Buffalow
Assistant Examiner—D. S. Nakarani
Attorney, Agent, or Firm—Finnegan, Henderson, Farabow, Garrett and Dunner

[57] ABSTRACT

Magnetizable composite microspheres comprising a core of a magnetizable filler distributed uniformly in a network of a polysilsesquioxane SiVi containing double bonds and a shell of a crosslinked organosilicon polymer derived from the hydrosilylation of an organohydrogenopolysiloxane SiH with the ethylenically unsaturated groups of the polysilsesquioxane. The magnetizable composite microspheres are obtained by dispersing an aqueous suspension of a magnetizable filler, not coated with a dispersing agent, in a solvent, dissolving an alkoxysilane or an alkoxysiloxane containing double bonds, polycondensing to a SiVi group-containing polysilsesquioxane SiVi, removing water, dissolving the organohydrogenopolysiloxane SiH polymer in the organic phase, crosslinking the mixture of polymers, removing water, separating the microspheres and, if appropriate, redispersing the microspheres in water. The magnetizable composite microspheres are preferably used as an active supports in biology.

13 Claims, No Drawings

MAGNETIZABLE COMPOSITE MICROSPHERES BASED ON A CROSSLINKED ORGANOSILICON POLYMER

The present invention relates to magnetizable composite microspheres based on a crosslinked organosilicon polymer, either alone or in an aqueous dispersion, a process for their preparation, and their application to biology.

In French Patent Application No. 2,624,873, the assignee of the present invention described magnetizable composite particles based on crosslinked organopolysiloxane, said particles consisting of a matrix originating from the hydrosilylation of an organopolysiloxane SiVi and an organohydrogenopolysiloxane SiH and, encapsulated in this matrix, magnetizable fillers coated with a dispersing agent insoluble in water. The presence of this dispersing agent can be a drawback for use in biology because the agent can migrate towards the surface of the particles and give rise to side reactions.

Applicants have now found composite microspheres of which the core comprises a magnetizable filler not coated with a hydrophobic surfactant and distributed uniformly inside a polysilsesquioxane network.

According to applicants' invention, the microspheres concerned are magnetizable composite microspheres based on a crosslinked organosilicon polymer, either alone or in aqueous dispersion, each microsphere comprising:

(1) a core comprising a) a magnetizable filler having a size smaller than $300 \times 10^{-4}$ μm, preferably ranging from $50 \times 10^{-4}$ to $120 \times 10^{-4}$ μm, distributed uniformly within a network of b) polysilsesquioxane SiVi containing, per molecule, at least two ethylenically unsaturated SiVi groups each bonded to a silicon atom or to a carbon atom of an organic group linked to the polysilsesquioxane chain by a Si—C bond, optionally carrying a non-ethylenic ionic and/or reactive unit bonded to a silicon atom or to a carbon atom of a hydrocarbon group linked to the polysilsesquioxane chain by a Si—C bond; and (2) a shell comprising a crosslinked organosilicon polymer derived from the hydrosilylation of a) an organohydrogenopolysiloxane SiH, containing, per molecule, at least three SiH groups with each comprising a hydrogen atom linked to a silicon atom, and having a viscosity ranging from 5 to 1,500 mPas at 25° C., preferably from 20 to 150 mPas at 25° C., and optionally carrying non-vinyl ionic and/or reactive units bonded to a silicon atom or to a carbon atom of a hydrocarbon group linked to the organohydrogenopolysiloxane chain by a Si—C bond, with b) the ethylenically unsaturated SiVi groups of said polysilsesquioxane SiVi.

Among the materials which can make up the magnetizable filler, the following may be mentioned by way of example: magnetite, hematite, chromium dioxide, and ferrites such as the manganese, nickel, and manganese-zinc ferrites. The preferred materials are magnetite and hematite. The magnetizable filler can also be a mixture of fillers. These materials may also be present as a mixture with a filler having a fluorescence spectrum such as yttrium oxide or oxysulphide activated with europium, gadoliniumcerium-terbium borate, cerium-terbium aluminate, magnesium-barium aluminate doped with divalent europium.

The amount of magnetizable filler corresponds to about 0.25 to 95% of the weight of the microspheres, and preferably from 4 to 76% of the weight; that of an optional fluorescent filler corresponds to 0.01 to 0.5% of the weight of the microspheres.

The polysilsesquioxanes SiVi can be obtained by polycondensation of an alkoxysilane of the formula:

$$R-Si-(OR')_3 \qquad (I)$$

or of an alkoxysiloxane of the formula:

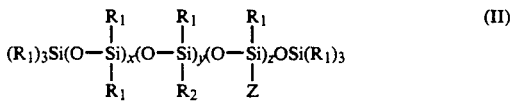

$$(R_1)_3Si(O-\underset{\underset{R_1}{|}}{\overset{\overset{R_1}{|}}{Si}})_x(O-\underset{\underset{R_2}{|}}{\overset{\overset{R_1}{|}}{Si}})_y(O-\underset{\underset{Z}{|}}{\overset{\overset{R_1}{|}}{Si}})_zOSi(R_1)_3 \qquad (II)$$

in which formulae:

the $R_1$ radicals are identical or different and are selected from $C_1$–$C_3$ alkyl radical, preferably methyl or ethyl, and a phenyl radical;

the $R_2$ radical is selected from a $C_1$–$C_3$ alkyl radical, a phenyl radical and a $C_1$–$C_4$ alkyl radical substituted by, for example, amino, epoxy, mercapto, or halogeno groups, preferably aminopropyl, glycidylpropyl, mercaptopropyl, bromopropyl, chloropropyl, or trifluoropropyl and the like, and a vinyl radical, number of vinyl radicals being at least two per molecule;

R is selected from a vinyl radical and an ethylenically unsaturated radical, preferably an unsaturated ester such as methacryloxypropyl;

OR' is selected from an OH radical and a hydrolyzable radical such as those in which R' represents a $C_1$–$C_4$ alkyl radical, or a —CO—CH$_3$, —CO—C$_2$H$_5$, —CO—CH$_2$—CO—CH$_3$, —CH$_2$—CH$_2$OH, —CH$_2$CH$_2$—OCH$_3$, or —CH$_2$—CH$_2$—OC$_2$—H$_5$ radical.

Z is a radical —r—Si(R$_1$)$_{3-n}$(OR')$_n$ in which r is a $C_1$–$C_{18}$, preferably a $C_2$–$C_6$, alkylene group and n is an integer from 0 to 3; and x, y and z have values sufficient to provide a viscosity less than 100 mPas at 25° C., wherein x or y can independently be zero.

The organohydrogenopolysiloxane SiH can be a straight-chain, branched, or cyclic polymer.

The preferable organohydrogenopolysiloxanes SiH are those of formula III:

$$Y (R_1)_2 SiO (R_1 R'' SiO)_p (Y R_1 SiO)_q Si (R_1)_2 Y \qquad (III)$$

wherein the $R_1$ radicals are identical or different and are selected from a $C_1$–$C_3$ alkyl radical and a phenyl radical, with at least 80% being methyl radicals; the radicals Y are identical or different and are selected from a $C_1$–$C_3$ alkyl radical, a phenyl radical and a hydrogen atom, the number of hydrogen atoms being at least 3 per molecule of polymer; the R'' radicals are identical or different and are selected from a $C_1$–$C_3$ alkyl radical, a phenyl radical, and a $C_1$–$C_4$ alkyl radical substituted by a reactive or ionic group, such as an amino, epoxy, mercapto, halogeno, preferably aminopropyl, glycidylpropyl, mercaptopropyl, bromopropyl, chloropropyl, or trifluoropropyl; p and q having values sufficient to provide a polymer having a viscosity ranging from 5 to 1,500 mPas at 25° C., preferably from 20 to 150 mPas at 25° C., and wherein the total number of units are selected from a non-vinyl ionic unit and/or a reactive unit contributed by the SiVi and SiH ranges from 1 to 1,000 per molecule, preferably from 5 to 500 per molecule, of SiH and SiVi.

The organohydrogenopolysiloxane polymers which do not contain a non-vinyl ionic and/or reactive unit are well known. They are described, for example, in U.S. Pat. Nos. 3,220,972, 3,344,111 and 3,436,366.

The organohydrogenpolysiloxane SiH polymers containing a non-vinyl ionic and/or reactive unit can be prepared by well-known methods.

The organohydrogenopolysiloxane SiH polymers containing a non-vinyl ionic and/or reactive unit can be obtained, for example, by:

equilibration of a cyclotetrasiloxane and a polysiloxane oil containing internal SiH groups in the presence of a disiloxane containing functional groups not reactive towards SiH groups, equilibration of a cyclotetrasiloxane containing functional groups, not reactive towards SiH groups, in the presence of a dihydrogenodisiloxane, equilibration of a polysiloxane oil containing functional groups, not reactive towards SiH groups, in the presence of a dihydrogenodisiloxane or of a polysiloxane containing internal SiH groups.

In one preferred embodiment of applicants' invention, the number-ratio of SiH groups (a hydrogen atom bonded to a silicon atom) to the SiVi groups (an ethylenically unsaturated group bonded directly or indirectly to a silicon atom) is between 0.75:1 and 4:1, preferably between 0.75:1 and 1.5:1.

The ratio by weight of the organohydrogenopolysiloxane SiH to the polysilsesquioxane SiVi can range from about 5:100 to 100:100, preferably from about 5:100 to 30:100.

The magnetizable microspheres which are the subject of applicants' invention are substantially spherical; they can be of uniform size or have a particle size variation; their diameter can range from about 0.05 to 3 microns, preferably 0.2 to 2 microns.

The magnetizable microspheres can be used alone or in a dispersion in water; the amount of magnetizable microspheres in the dispersed state in water can correspond to about 10 to 70% by weight, relative to the total weight of dispersion, and preferably on the order of 15 to 50% by weight.

The magnetizable composite microspheres which are the subject of applicants' invention can be prepared by a process comprising:

dispersing in a water-immiscible organic solvent, an aqueous suspension of a magnetizable filler, not coated with a dispersing agent, said filler having a size preferably smaller than $300 \times 10^{-4}$ μm, more preferably from $50 \times 10^{-4}$ to $120 \times 10^{-4}$ μm;

dissolving an alkoxysilane of formula I or an alkoxysiloxane of formula II, capable of undergoing polycondensation to form a polysilsesquioxane SiVi, containing, per molecule, at least two ethylenically unsaturated SiVi groups, each bonded to a silicon atom or to a carbon atom of an organic group linked to the polysilsesquioxane chain by a Si—C bond;

subjecting said alkoxysilane or alkoxysiloxane to polycondensation to form a polysilsesquioxane SiVi;

removing the water resulting from the polycondensation;

dissolving in the organic phase of the dispersion obtained, a) at least one organohydrogenopolysiloxane SiH containing, per molecule, at least three SiH groups with each comprising a hydrogen atom linked to a silicon atom, having a viscosity ranging from about 5 to 1,000 mPas at 25° C., preferably 20 to 150 mPas at 25° C., and optionally carrying non-vinyl ionic and/or reactive units bonded to a silicon atom or to a carbon atom of a hydrocarbon group linked to the organohydrogenopolysiloxane chain by a Si—C bond, and b) a hydrosilylation catalyst;

crosslinking the mixture of polysilsesquioxane SiVi and organohydrogenopolysiloxane SiH polymers;

separating off the magnetizable microspheres;

and, if appropriate, redispersing said microspheres in water.

One preferred process comprises introducing all or part of an alkoxysilane or an alkoxysiloxane into the aqueous suspension of a magnetizable filler before dispersing said aqueous suspension in the organic solvent.

The organic solvent used in the dispersion step is a solvent for alkoxysilanes of formula I or alkoxysiloxanes of formula II. The following may be mentioned by way of example: cyclohexane, methylene chloride, benzene, hexane, toluene, carbon tetrachloride, octane and esters of fatty diacids.

The dispersion step is preferably carried out in one or more steps at a temperature ranging from about 20° C. to 60° C., with the aid of a vigorous agitation system, such as a colloid mill, high-pressure pumps, a vibratory stirrer, or ultrasonic equipment.

The aqueous suspension of a magnetizable filler can be obtained by suspending a filler which has been ground up; however, a preferential form of suspension is an aqueous sol of a magnetizable filler obtained by any known process, such as that described in U.S. Pat. No. 3,480,555.

The concentration of magnetizable filler in the aqueous suspension can range from about 0.5 to 50% by weight, preferably about 5 to 20% by weight. The amount of filler used is such that the ratio, by weight, of magnetizable filler to alkoxysiloxane or alkoxysilane ranges from about 0.005:1 to 50:1.

The amount of organic solvent used is such that the ratio, by weight, of the aqueous phase to the organic phase ranges from about 0.005:1 to 2:1.

A surfactant is used to carry out the dispersion step. The surfactant is preferably chosen from those enabling the attainment of a water-in-oil emulsion having an HLB generally lower than 10 and preferably lower than 5. Such surfactants may be selected from the nonionic agents of the type of fatty acid esters of sorbitol, sorbitan mono- and tri-oleates, ethylene oxide/propylene oxide block copolymers, ethoxylated alkylphenols containing less than 10 ethoxylated units, polycondensation products of fatty acids, and organosiloxane—ethylene oxide—propylene oxide block copolymers; anionic agents, such as dialkyl sulphosuccinates; and cationic agents, such as cetylammonium bromide and polyethyleneimine-polyester copolycondensation products.

The polycondensation step is preferably carried out at a temperature ranging from 20° C. to 80° C. for about 5 to 24 hours.

The water is then removed, for example, by distillation.

Compounds which may be used as silylation catalyst are compounds of a metal of the platinum group, preferably their salts and complexes, especially chloroplatinic acid and the platinumolefin complexes as described in the U.S. Pat. Nos. 3,159,601 and 3,159,662, the products of the reaction of derivatives of platinum with alcohols, aldehydes and ethers described in U.S. Pat. No. 3,220,972, the platinum-vinylsiloxane catalysts described in French Patent No. 1,313,846 and its addition 88,676 and French Patent No. 1,480,409 and also the complexes described in the U.S. Pat. Nos. 3,715,334, 3,775,452 and 3,814,730 and a rhodium catalyst as described in U.S. Pat. Nos. 3,296,291 and 3,928,629.

The preferred metals of the platimun group are platinum and rhodium. Ruthenium, which is less active and less expensive than platinum or rhodium, can also be used.

The amount of catalyst used can range from about 5 to 100 ppm, preferably 10 to 60 ppm, calculated as weight of metal relative to the total weight of the organohydrogenopolysiloxane SiH and polysilsesquioxane SiVi polymers.

In a preferred embodiment of the invention, the relative amounts of the SiH and SiVi polymer are such that the number-ratio of SiH groups (hydrogen atom bonded to a silicon atom) to the SiVi groups (ethylenically unsaturated group bonded directly or indirectly to a silicon atom) ranges between 0.75:1 and 4:1, preferably between 0.75:1 and 1.5:1, and the ratio by weight of the organohydrogenopolysiloxane SiH to the polysilsesquioxane SiVi ranges between 5:100 and 100:100, preferably 5:100 and 30:100.

The crosslinking step can be carried out at a temperature ranging from 20° C. to 90° C., preferably 50° C. to 70° C. This step generally takes about 2 to 24 hours.

The water is then removed, for example, by distillation.

After cooling, the magnetizable microspheres can be separated from the organic medium by any known means, preferably by magnetization.

If desired, said magnetizable microspheres can be redispersed in deionized water until a proportion of solids of about 10 to 70% by weight, preferably of the order of 15 to 50% by weight, is obtained. This operation is carried out in the presence of at least one surfactant, such as an alkylsulphate or an alkysulphonate enabling the attainment of an oil-in-water emulsion having an HLB generally higher than 10, preferably higher than 15.

The magnetizable microspheres which are the subject of applicants' invention are of particular value in biology.

The magnetizable microspheres can be used, for example, as active supports:

for antibodies or antigens for diagnostics tests, the separation of biological compounds by affinity; the fixation of biological molecules can, if necessary, be carried out by well-known coupling methods involving coupling agents (glutaraldehyde, water-soluble carbodiimide), or by activating any groups in the polyorganosiloxane (for example by diazotization, by the action of cyanogen bromide or hydrazine) and for reacting the molecule to be fixed;

for enzymatic systems for biological reactions;

for fixation of cell cultures;

to guide medicaments or indicator substances towards the chosen point of treatment either in vitro or in vivo;

for chemical molecules enabling growth of these molecules by rapid sequences of individual reactions, such as peptide synthesis;

for reaction catalysts;

for the separation or the extraction of metals or optical isomers.

Said microspheres can also be used as reinforcing fillers for elastomers or for the preparation of organic dispersions used in the hydraulic circuits of brakes and shock absorbers.

When the microspheres contain a luminescent filler, said microsphere can be used as a cell marker or as a contrast agent in medical imagery.

The following examples are given by way of illustration and may not be regarded as limiting the field and the spirit of the invention.

The aqueous suspension of magnetic iron oxide, not treated with a surfactant, used in the examples below, was prepared in the following way: 175 g of Fe($NO_3$)$_3$.9H$_2$O and 75 g of Fe(SO$_4$).7H$_2$O were dissolved in 250 g of ion-exchanged water and 55 g of concentrated nitric acid; 250 g of a 20% aqueous solution of ammonia were added while stirring vigorously. After settling and removing the supernatant solution, the precipitate was washed once with water. The mixture was then adjusted to pH 0.5 by means of 35 g of perchloric acid, and the precipitate was filtered off; this operation was repeated 3 times, after which the oxide was re-suspended in water and subjected to ultrafiltration by means of ion-exchanged water. The suspension thus obtained had a solids content of 26.5% at a pH of 1.2. The yield expressed as Fe$_3$O$_4$ was 57%. Examination by transmission electron microscopy indicated iron oxide particle sizes of between $50 \times 10^{-4}$ and $200 \times 10^{-4}$ microns

EXAMPLE 1

Preparation of magnetizable microspheres based on poly(vinyl)silsesquioxane 1.4 g of the iron oxide suspension prepared above was diluted with 0.6 g of water; the whole was dispersed in a mixture comprising of 50 g of octane and 0.1 g of SPAN 80 (sorbitan monooleate marketed by ICI (UK)), with the aid of an ultrasonic homogenizer. 2 g of vinyltrimethoxysilane (VTMO) were introduced into this inverse emulsion, which was then put into a 100 ml glass round-bottomed flask which was adapted to a rotary evaporator; the mixture was stirred by rotation at a temperature of 50° C. for 4 h and then for another hour at 80° C. in order to progressively drive off the water by azeotropic distillation. The particles were isolated by magnetic separation and washed with 30 g of octane. The amount of particles recovered was 1.25 g, which was a polycondensation yield of 83%, expressed as weight of poly(vinyl)silsesquioxane formed The iron oxide content of the particles was 30% by weight, estimated by determination of iron by atomic absorption; the particle sizes were between 0.1 micron and 0.5 micron, measured by transmission electron microscopy.

EXAMPLE 2

Example 1 was repeated except that the vinyltrimethoxysilane (VTMO) was replaced by methacryloxypropyltrimethoxysilane (MEMO). The yield, expressed as weight of poly(methacryloxypropyl)silsesquioxane formed, was 42%. The iron oxide content of the particles was 47%.

EXAMPLE 3

Preparation of magnetizable "core-shell" microspheres comprising an Fe$_3$O$_4$/poly(vinyl)silsesquioxane core and a crosslinked polydimethylsiloxane shell The microspheres prepared in Example 1 were dispersed in 30 g of octane in the presence of 0.1 g of SPAN 80; 2 g of a hydrosilylated organosilicon oil of formula:

$$R''R'RSiO-(SiRR'''O)_n-(SiR'''R'O)_m-SiRR'R'',$$

where: $R=R'=R'''=-CH_3$, $R''=-CH:CH_2$
with $n+m=142$ and 2 drops of platinum catalyst (Pt(divinyltetramethyldisiloxane)$_2$ complex) were then added.

The whole was then put into a 100 ml glass round-bottomed flask which was adapted to a rotary evaporator; the mixture was stirred by rotation, at a temperature of 50° C. for 3 hours. The particles were then recovered by magnetic settling and dispersed in a 90/10 water-/acetone mixture in the presence of Cemulsol NP 30 (ethoxylated nonylphenol containing 30 molecules of ethylene oxide, marketed by SFOS (France)) in a concentration of 1 g/l; the residual octane was driven off by azeotropic distillation. The amount of particles recovered was 2.4 g, which was a hydrosilylation yield of 57%, expressed as weight of crosslinked polydimethylsiloxane at the surface of the particles. The iron oxide content of the particles was 17% by weight and the sizes of the core-shell particles were between 0.2 micron and 0.8 micron, measured by transmission electron microscopy.

EXAMPLE 4

Preparation of magnetizable "core-shell" microspheres comprising an Fe$_3$O$_4$/poly(methacryloxypropyl)-silsesquioxane core and a crosslinked polydimethylsiloxane shell The conditions of Example 3 were employed, except with the microspheres prepared according to Example 2. The hydrosilylation yield was 60%, expressed as weight of crosslinked polydimethylsiloxane at the surface of the particles. The iron oxide content of the particles was 16% by weight.

EXAMPLE 5

Preparation of magnetizable "core-shell" microspheres comprising an Fe$_3$O$_4$/poly(vinyl)silsesquioxane core and a shell of crosslinked polydimethylsiloxane containing epoxy functional groups The conditions of Example 3 were employed with the microspheres employed according to Example 1, except that the hydrosilylated organosilicon oil was replaced by a hydrosilylated and epoxidized organosilicon oil of formula:

$$R'_3SiO-(SiRR''O)_o(SiRR'''O)_p-(SiYRO)_q-SiR'_3,$$

where $R-R'=R''=-CH_3$, $Y=H$, $R'''=$ glycidyl ether
with $o=33$, $p=6$, $q=6$

The hydrosilylation yield was 33%, expressed as weight of crosslinked epoxidized polymethylsiloxane at the surface of the particles. The iron oxide content of the particles was 20%.

EXAMPLE 6

Preparation of magnetizable "core-shell" microspheres comprising an Fe$_3$O$_4$/poly(vinyl)silsesquioxane core and a shell of crosslinked polydimethylsiloxane containing an amine functional group 1 g of the microspheres prepared in Example 5 were taken and redispersed in 25 g of toluene. The dispersion was then charged into a thermo-controlled 100 ml glass reactor fitted with a stirrer and a condenser. The temperature was brought to 100° C.; 0.8 g of an alkoxylated diamine of formula:

$$H_2N-CH(CH_3)CH_2-[O-CH(CH_3)CH_2]_a-[OCH_2CH_2]_b-[O-CH(CH_3)CH_2]_c-NH_2$$

with $a+c=2.5$ and $b=8.5$ (Jeffamine, marketed by Texaco (USA)) was then added dropwise.

The reaction mixture was left at this temperature for 15 hours. After cooling, the excess amine was removed by magnetic settling. The animated microspheres were then redispersed in water in order to obtain a magnetizable latex.

EXAMPLE 7

Comparative Example for Example 1

In this example the aqueous suspension of iron oxide not treated with a surfactant, as described above, was replaced with a suspension of iron oxide treated with a surfactant and prepared by the process claimed in U.S. Pat. No. 4,094,804; which involves iron oxide precipitated in the presence of oleic acid, which was repeptized in an aqueous medium by adding anionic emulsifier (dioctyl sulphosuccinate, Aerosol OT marketed by American Cyanamid). The synthesis was continued as indicated in Example 1: in this example magnetizable microspheres were not obtained; in fact, the iron oxide had diffused progressively from the aqueous phase towards the organic phase.

What is claimed is:

1. Magnetizable composite microspheres, comprising:
   (1) a core consisting essentially of a) a magnetizable filler having a size smaller than about $300 \times 10^{-4}$ μm, distributed uniformly within a network of b) polysilsesquioxane SiVi containing, per molecule, at least two ethylenically unsaturated SiVi groups, each bonded to a silicon atom or to a carbon atom of an organic group linked to the polysilsequioxane by a Si—C bond; and
   (2) a shell comprising a crosslinked organosilicon polymer derived from the hydrosilylation of a) an organohydrogenopolysiloxane, containing, per molecule, at least three SiH groups with each comprising a hydrogen atom linked to a silicon atom, and having a viscosity ranging from 5 to 1,500 mPas at 25° C. with b) the ethylenically unsaturated SiVi groups of said polysilsesquioxane.

2. Microspheres according to claim 1, wherein the polysilsesquioxane contains at least one unit selected from the group consisting of a non-ethylenic ionic unit and a reactive unit bonded to a silicon atom or to a carbon atom of a hydrocarbon group linked to the polysilsesquioxane by a Si—C bond.

3. Microspheres according to claim 1, wherein the organohydrogenopolysiloxane contains at least one unit selected from the group consisting of a non-ethylenic ionic unit and a reactive unit bonded to a silicon atom or to a carbon atom of a hydrocarbon group linked to the polysilsesquioxane by a Si—C bond.

4. Microspheres according to claim 1, wherein both the organohydrogenopolysiloxane and polysilsesquioxane contain at least one unit selected from the group consisting of a non-ethylenic ionic unit and a reactive unit bonded to a silicon atom or to a carbon atom of a hydrocarbon group linked to the SiH and SiVi by a Si—C bond.

5. Microspheres according to claim 1, wherein said magnetizable filler has a size ranging from about $50 \times 10^{-4}$ to $120 \times 10^{-4}$ μm.

6. Microspheres according to claim 1, wherein the amount of magnetizable filler is about 0.25 to 95% of the weight of the microspheres.

7. Microspheres according to claim 1, wherein the number-ratio of SiH groups to the SiVi groups ranges from about 0.75:1 to 4:1.

8. Microspheres according to claim 1, wherein the ratio, by weight, of organohydrogenopolysiloxane to polysilsesquioxane ranges from 5:100 to 100:100.

9. Microspheres according to claim 1, wherein the polysilsesquioxane is derived from the polycondensation of an alkoxysilane of the formula:

(I)

or an alkoxysiloxane of the formula:

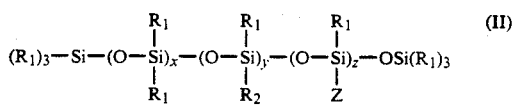
(II)

in which formulae:
- R is selected from the group consisting of a vinyl radical and an ethylenically unsaturated radical;
- the $R_1$ radicals are identical or different and are selected from the group consisting of a $C_1$-$C_3$ alkyl radical and a phenyl radical;
- the $R_2$ radical is selected from the group consisting of a $C_1$-$C_3$ alkyl radical, a phenyl radical and a $C_1$-$C_4$ alkyl radical substituted by reactive groups, ionic groups or a combination thereof and a vinyl radical, the number of vinyl radicals being at least two per molecule;
- OR' is selected from the group consisting of an OH radical and a hydrolyzable radical wherein R' represents a $C_1$-$C_4$ alkyl radical or a —CO—CH$_3$, —CO—C$_2$H$_5$, —CO—CH$_2$—CO—CH$_3$, —CH$_2$—CH$_2$OH, —CH$_2$CH$_2$—OCH$_3$ or —CH$_2$—CH$_2$—OC$_2$—H$_5$ radical;
- Z is a radical —r—Si($R_1$)$_{3-n}$(OR')$_n$ in which r is a $C_1$-$C_{18}$ alkylene group and n is an integer from 0 to 3; and
- x, y and z have values sufficient to provide a viscosity less than 100 mPas at 25° C., wherein x or y can independently be zero.

10. Microspheres according to claim 4, wherein the reactive group, the ionic group or a combination thereof is selected from the group consisting of amino, epoxy, mercapto and halogeno groups.

11. Microspheres according to claim 1, wherein the organohydrogenopolysiloxane has the formula:

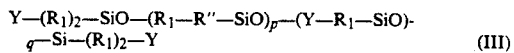
(III)

wherein the $R_1$ radicals are identical or different and are selected from the group consisting of a $C_1$-$C_3$ alkyl radical and a phenyl radical, with at least 80% being methyl radicals; the radicals Y are identical or different and are selected from the group consisting of a $C_1$-$C_3$ alkyl radical, a phenyl radical and a hydrogen atom, the number of hydrogen atoms being at least 3 per molecule of polymer; the R" radicals are identical or different and are selected from the group consisting of a $C_1$-$C_3$ alkyl radical, a phenyl radical, and a $C_1$-$C_4$ alkyl radical substituted by a reactive group, an ionic group or a combination thereof; and p and q having values sufficient to provide a polymer having a viscosity ranging from 5 to 1,500 mPas at 25° C.

12. Microspheres according to claim 4, wherein the organohydrogenopolysiloxane has the formula:

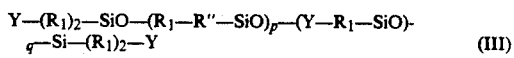
(III)

wherein the $R_1$ radicals are identical or different and are selected from the group consisting of a $C_1$-$C_3$ alkyl radical and a phenyl radical, with at least 80% being methyl radicals; the radicals Y are identical or different and are selected from the group consisting of a $C_1$-$C_3$ alkyl radical, a phenyl radical and a hydrogen atom, the number of hydrogen atoms being at least 3 per molecule of polymer; the R" radicals are identical or different and are selected from the group consisting of a $C_1$-$C_3$ alkyl radical, a phenyl radical, and a $C_1$-$C_4$ alkyl radical substituted by a reactive and/or ionic group; p and q having values sufficient to provide a polymer having a viscosity ranging from 5 to 1,500 mPas at 25° C., and wherein the total number of units are selected from a nonvinyl ionic unit, a reactive unit or a combination thereof contributed by the polysilsesquioxane and organhydrogenopolysiloxane ranges from 1 to 1,000 per molecule thereof.

13. Microspheres according to claim 1, having a particle size ranging from about 0.05 to 3 microns.

* * * * *